United States Patent [19]

Musha et al.

[11] 4,249,538

[45] Feb. 10, 1981

[54] ELECTRONIC CLINIC APPARATUS

[75] Inventors: Toshimitsu Musha, 13-17, Minami-Tsukushino 2-chome, Machida-shi, Tokyo; Kenichi Harumi, 36-5, Takadanobaba 3-chome, Shinjuku-ku, Tokyo; Yasuaki Teramachi, Kokubunji; Toshiyuki Kanou, Koganei, all of Japan

[73] Assignees: Toshimitsu Musha; Kenichi Harumi, both of Japan

[21] Appl. No.: 968,854

[22] Filed: Dec. 12, 1978

[30] Foreign Application Priority Data

Oct. 24, 1978 [JP] Japan ................. 53-130001

[51] Int. Cl.³ .............................................. A61B 5/04
[52] U.S. Cl. ................. 128/630; 128/639; 128/696; 128/709; 364/415
[58] Field of Search ............... 128/630, 639, 640, 695, 128/696, 699, 709, 710, 712; 364/415, 417

[56] References Cited

U.S. PATENT DOCUMENTS

| | | | |
|---|---|---|---|
| 3,294,084 | 12/1966 | Schuler et al. | 128/712 |
| 3,387,608 | 6/1968 | Figar | 128/640 |
| 3,518,696 | 6/1970 | Tomota et al. | 128/710 |
| 3,620,208 | 11/1971 | Higley et al. | 128/639 |
| 4,115,864 | 9/1978 | Vick et al. | 128/702 |

OTHER PUBLICATIONS

Groom et al., "American Journal of Medical Electronics", Oct.-Dec., 1964, pp. 261-265.

*Primary Examiner*—William E. Kamm
*Attorney, Agent, or Firm*—Fleit & Jacobson

[57] ABSTRACT

An improved electronic clinic apparatus includes a group of a number of probes positioned on or above at least one body surface of a person subjected to a clinic operation. It includes further a multichannel amplifier for amplifying electrical potential sensed at each of the probes. A multiplexer is connected with the amplifier at its output and an AD-amplifier is connected with the multiplexer at its output. An electronic computer for treatment of digital outputs from the AD-amplifier is provided. Various and several display units are provided for displaying outputs from the computer. Control means are provided between the multiplexer and the computer for successive read-out of the sensed potentials at the grouped probes and within a variable operating period, and for providing a pause period thereafter. The variable operating period added with the pause period defines a predetermined functional cycle period such as 2 ms. The subject apparatus removes improper probe signal(s) including inhibitingly large noise signals and replenishes properly calculated and established imaginary signals in place thereof. The removal and replenishing job is performed during said pause period.

6 Claims, 18 Drawing Figures

ELECTRONIC CLINIC APPARATUS

BACKGROUND OF THE INVENTION

This invention relates to electronic clinic apparatuses, and more particularly, it relates to those adapted for electronic observation of a living organ and the like of human or animal bodies.

In the following description, it will be set forth in connection with a living heart of a human body. However, it should be understood that the invention should not be limited to heart disease clinic apparatuses, but it can be applied to other living organs such as kidney, liver, lungs, pancreas or brain.

Taking the electrocardiograph as an example, it represents a graph plotting a series of weak electromotive forces appearing at the living heart when it makes beats, against the time, and normally comprises so-called P-loop, QRS-loop, T-loop and U-loop or -wave. However, it has been experienced that only insufficient and rough information is given with such kind of electrocardiograph for making a precise and detailed clinic observation to find various heart diseases such as myocardinal infarcation, right bundle branch block, cardiac failure, specific or non-specific ST-abnormality, ischemic and/or spontaneous pneumothorax.

In the past, more specifically in 1963, Taccardi in Italy made such experiments that about 200 probes were set on a human body surface in the vicinity of the heart and the heart potentials as sensed by these probes were measured simultaneously and successively so as to represent a body surface potential contour diagram, by assuming the body surface to be a plane.

According to our studies, however, it has been found that with such sensing, measuring and signal treating method, much is desired to be added for obtaining enough clinic information necessary for the execution of precise shooting of possible existence of heart diseases, mainly on account of unavoidable significant amounts of outside and inside noise signals.

It has been further found that these noise signals take place from various and indeterminate causes. As an example, when the person under clinic treatment moves bodily for sneezing or the like, the sensing voltage at the probe will vary to a considerable degree. On the other hand, since the body surface under consideration is far from a pure plane, the degree of contact of the probe with the body may naturally differ, depending upon the local position of the probe. Even when the probe is of the electromagnetic type which is normally placed at a certain distance from the body surface, the separating distance may differ locally and occasionally. In addition, the amplifier which is connected with the probe may be subjected to an electric disorder. Further, electrical leads may be influenced capacitively and variously by outside electrical causes.

As a conclusion, one or more of these causes give rise to substantial amount of noises in comparison with relatively small values of sensed electrical potentials in random manner for each probe.

The main purpose of the present invention is to provide an efficient and reliable electronic clinic apparatus for shooting various heart diseases in their kind, location and even suffered degree, in spite of the very presence of the aforementioned considerable amounts of disturbing noise signals.

SUMMARY OF THE INVENTION

In the present invention, a large number of probes such as 64–200 pieces are arranged on the breast or back or on the both of the body surface of a patient as in the similar manner as adopted by Taccardi.

Each of these probes is electrically connected with an amplifier channel. These amplifier channels are electrically connected through a multiplexer with an AD-converter to convert the sensed and amplified analogue signals into digital ones. The multiplexer is so designed and arranged as to pick up the analogue signals successively and substantially in a definite order.

The output of the AD-converter is connected to an IC-memory which is connected with a microcomputer. Between the converter and the IC-memory, there is provided a preferably combined comparator and interpolator for comparing and occasionally interpolating the converted signals in a specific manner to be described.

A first control circuit is arranged to cooperate with the IC-memory and the microcomputer, and with the converter, so as to compare and interpolate the converted signals.

The first control circuit controls through a second controller the multiplexer for properly modifying the operation of the multiplexer in a specific way as will become more apparent as the description goes on.

This and further objects, features and advantages of the invention will become more apparent when the following detailed description of the invention is read with reference to the accompanying drawings in which:

PREFERRED EMBODIMENTS OF THE INVENTION

Referring now to the accompanying drawings, substantially a preferred embodiment of the present invention, together with modifications, will be set forth more in detail.

Figures 1A, 1B, 1C:
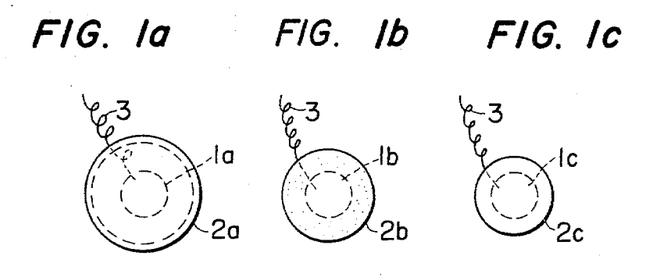
FIG. 1 is a schematic plan view of three different modes (a), (b) and (c) of a probe.

In FIG. 1, (a), (b) and (c), three different modes of the probe or sensing electrode are illustrated.

In FIG. 1 at (a), a sensing electrode proper 1a is shown only schematically which is positioned firmly on the body surface of a person under clinic treatment by means of a sucking cup 2a, the latter being illustrated only in a simplified manner. This probe unit is liable to be affected by least possible and disadvantageous drift when the human body is unavoidably moved. However, the patient may have an unpleasant feeling if the clinic treatment extends for a long time. Thus, this sensing unit is suitable for use in a short time clinic treatment.

In FIG. 1 at (b), a modified probe is shown which comprises a central electrode 1b surrounded by an adherent agent layer 2b for attachment onto the human body. It is very easy to attach this unit onto the body surface. However, the sensed potential may be subjected to unintentional alteration. It is advantageous, however, to set this unit on the rear side body surface. The patient can lie on a bed without trouble.

In a further modified probe shown in FIG. 1 at (c), the electrode 1c is fixedly attached onto the body surface by means of a sticking tape 2c.

In each of these embodiments of the probe, a lead 3 is connected at its one end with the probe as shown, while the opposite end of the lead extends to a respective amplifier element to be described.

As a result of practical measurement, the d.c. resistance of these probes was found to be 2–40 kiloohms at (a), 10–300 kiloohms at (b), and 30–100 kiloohms at (c) in FIG. 1, respectively. In practice, however, the corresponding a.c. resistance is substantially reduced by the presence of an equivalent capacitance Cs shown in FIG. 2.

Figure 2:
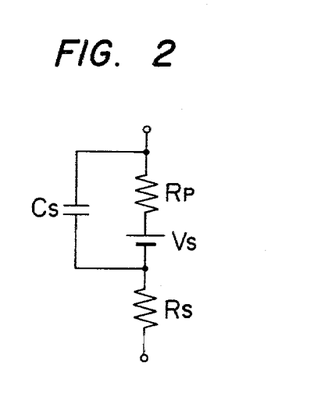
FIG. 2 is an equivalent circuit of a probe.

In FIG. 2, an equivalent circuit of the probe is shown. As a result of practical experiment, the input impedance of the preamplifier to be described amounts in the order of 1 megaohms. As shown, the circuit consists of a series connection of resistance Rp, contact potential difference Vs and further resistance Rs, and a parallel connection of the said capacitance Cs. The value of the capacitance Cs is negligibly small, on account of the small band frequency range of the cardiograph as a whole and a small time constant.

According to the practical measurement, the value of resistance Rs is also negligibly small. Therefore, both Rp and Vs should mainly be taken into account. Vs will give rise to a disadvantageous drift. According to our practical experiments, the value of Vs may frequently produce noise signals having frequencies within the frequency band of the preamplifier connected to the probe and in the course of initial several minutes only counted from the time of attachment of the latter to the body surface. Further, it has been experienced disadvantageously that the value of Vs varies with unavoidable movements of the patient's body to such a degree that noise signals having frequencies falling within the frequency band of the preamplifier are generated. However, by applying a conductive paste between the probe and the body surface, the value of Vs may be considerably reduced.

Figure 3:
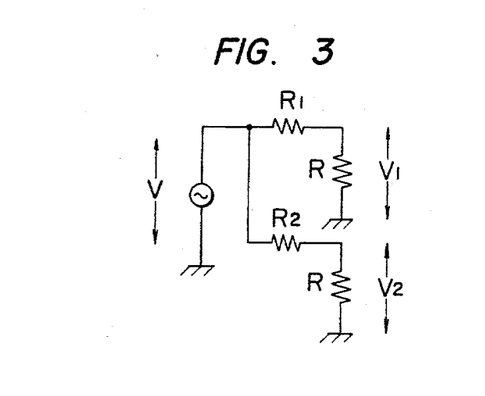
FIG. 3 is an equivalent circuit for the explanation of why electric noise signals will be generated through and around each of a number of probes.

Attention must be directed further to the fluctuation of Vs which is normally experienced and should be taken into account more appreciably than the value per se of Vs. For the evaluation of the fluctuation, an equivalent circuit as shown in FIG. 3 may be considered where V represents the cardinal electromotive force and R1 and R2 are contact resistance elements of the probe, while R represents input impedance at the preamplifier. Then, we obtain:

$$R2 = R1 + \Delta R1 \tag{1}$$

$$V2 = V\frac{R}{R2 + R1} = \frac{VR}{R1 + R + \Delta R1} \tag{2}$$

$$V1 = V\frac{R}{R1 + R} \tag{3}$$

$$\frac{V2}{V1} = \frac{R1 + R}{R1 + R + \Delta R1} \tag{4}$$

$$\approx 1 - \frac{\Delta R}{R1 + R} \tag{5}$$

When assuming that the error is represented by $\Delta R/(R1+R)$; $R1 < < R$, it may be $\Delta R/R$. Since the input impedance of the preamplifier may be 1 megaohm and the error at the probe may be 1%, the fluctuation of probe resistance will be ±5 kiloohms. This degree of fluctuation value will appear under optimal contacting condition of the probe and it will become substantially larger if the probe fails in contact with the body surface. These substantial errors will induce naturally corresponding false signals which must, therefore, be removed from the sensed signal series and, instead, new and correctly assumed signals must be introduced, as will be later more fully described.

In the foregoing description, the description is made only of a single probe. In practice, however, for making a precise measure of the body surface potentials, a larger number of probes, such as 8×8=64, must be used. Further, the following requirements must be satisfied as far as possible:

(a) low as possible probe contact resistance;

(b) constant as possible probe contant resistance for an extended period;

(c) mental and physical easement of the patient holding the probes;

(d) possibility of ease and prompt attachment of the probes; and (e) ease and undisturbed on-bed-treatment of the patient who carries the probes.

Figure 4:
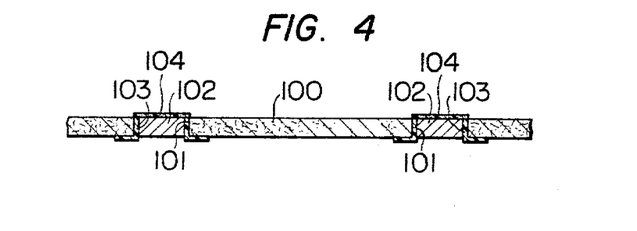
FIG. 4 is a sectional view of a part of a common support of the probes preferably usable in the invention.

For this purpose, we recommend a grouped probe arrangement, as shown in FIG. 4, comprising an insulating and flexible mat 100' made of a felt, as an example, and having a thickness of 2–3 milimeters or so. This mat may preferably be a square of 50×50 centimeters, punched with 8×8=64 holes 101. Each of these is inserted with a probe 102 through the intermediary of a sticking polymer layer 103. The probe substantially may have a diameter of 10 milimeters. The leads 3 have been omitted from this drawing only for convenience. On the working end surface of the probe, a conductive paste 104 is coated as shown.

Figure 5A:
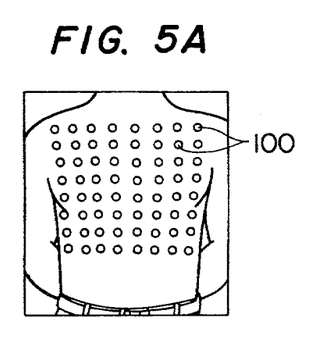
FIG. 5 represents two arrangements (A) and (B) of a group of probes set on the breast and back of a patient.
Figure 5B:
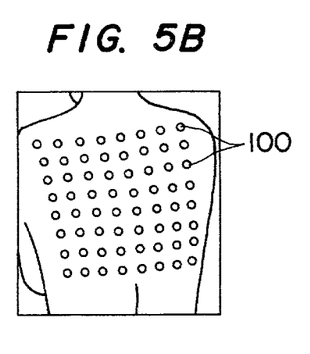

In FIG. 5 at (A), there are shown only schematically 8×8=64 probes 100 attached onto the breast of a person in the vicinity of his heart, while in FIG. 5 at (B), the same number of probes 100 are attached onto his back surface, correspondingly. If desired, however, only one set of probes will do in place of the two side arrangements. The number of the probes may be increased to, say, 200 pieces. In a still modified probe arrangement, 100 pieces on one side and 64 pieces on the other side of the person will do also. There may be 30 pieces and 40 pieces arranged on the breast and back surfaces of the person.

In place of the contact type probes, electromagnetic probes may be used. In this case, the probe is set at a certain distance from the body surface. The electromagnetic probe is commercialized under the trade name "Squid" which comprises a niob wire coil which is mounted in a hermetically sealed cylindrical vessel of about 20 milimeter diameter and filled with helium gas held at 9° K. This probe unit is capable of sensing even the slightest change of the magnetic field by the superconductive activity.

Figure 6:
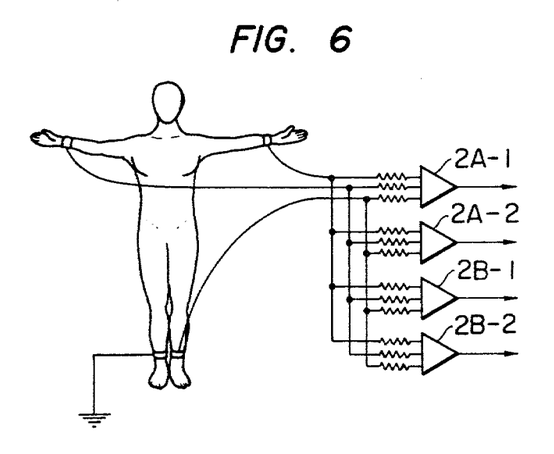
FIG. 6 is a schematic representation how the earthed side of the apparatus is connected through the body of the patient.

In FIG. 6, a connection mode of negative sides of preamplifiers 2A-1, 2A-2, 2B-1 and 2B-2 is shown, wherein only each two channels of the preamplifiers 2A and 2B to be described being representively depicted. As shown, two hands and a leg are connected with the preamplifiers, while the remaining leg is earthed.

Figure 7:
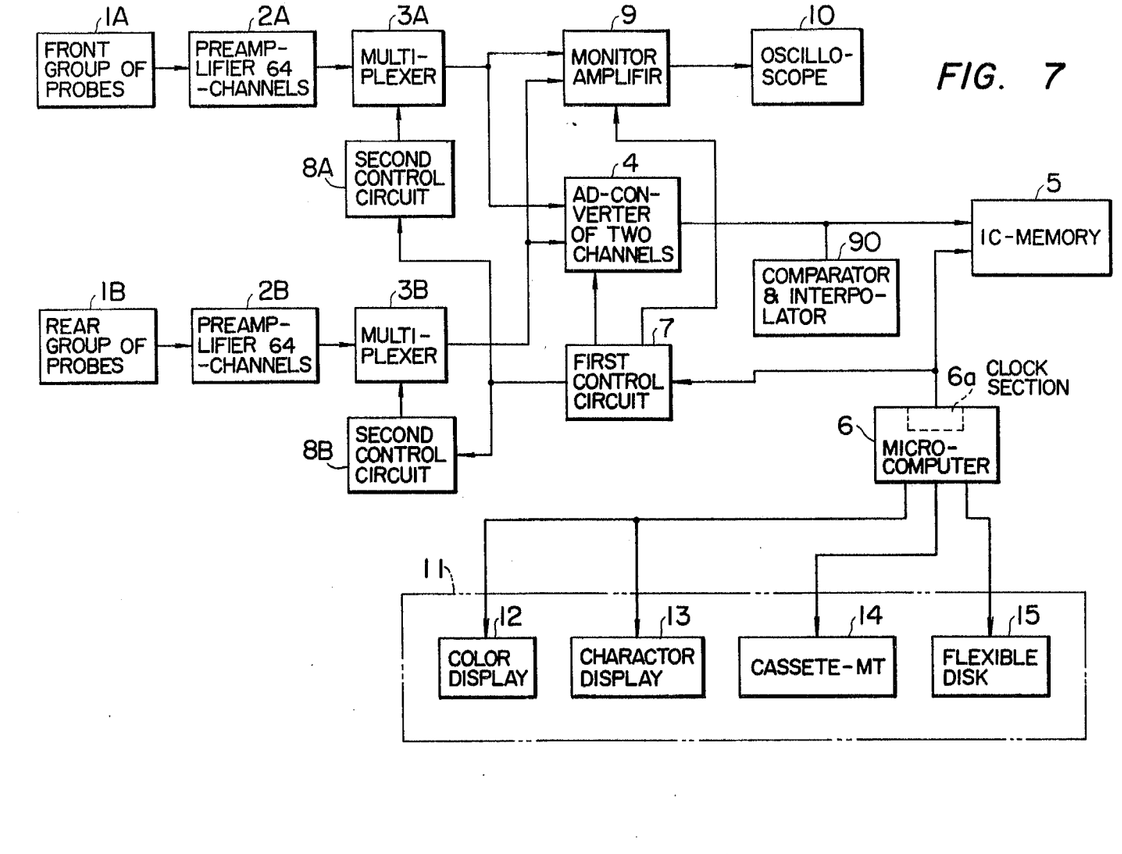
FIG. 7 is a block diagram showing several main constituents of the apparatus.

In FIG. 7, the block 1A represents the group of probes arranged on the breast surface of a person, while the block 1B represents the group of probes set on the back surface of the same person. The probes are arranged to have a mutual horizontal distance of 4.5 centimeters. The probes are arranged to have the same vertical mutual distance. However, these dimensions must not be precise and, thus, they may be arranged only roughly. As was already referred to in FIG. 3, the number of probes is selected to be 64 on each side of the body surface.

If desired, the mutual horizontal distance of probes may be increased to 8 centimeters or so on one body surface, so as to reduce the number of probes correspondingly, without sacrificing, substantially the functional performance.

Block 2A represents a first preamplifier of multichannel type, each of the latter being connected with one of the probes arranged on the breast, while 2B represents second parallel preamplifier again of multichannel type, each of the latter being connected with one of the probes arranged on the body back. These preamplifiers 2A and 2B have been so designed and arranged as to amplify several milivolts signal sensed at each probe to several volts or so. These input signals may be changed off to 1-, 2- or 4 milivolts range. In this way, the preamplifier 2A or 2B comprises 64 preamplifier channels. The reason why such preamplifier channels are provided a in place of a comman one, is to improve the signal-to-noise ratio appearing at the next following multiplexer 3A or 3B.

Since, in practice the contact resistances at the probes are not identical and, thus, corresponding signal errors will be fed therefrom to the respective preamplifier channels. However, with the use of such preamplifier channels, the influence of such error signals may be limited to the corresponding one or more only. However, in the case of the electromagnetic type probes, there is no problem of the difference in the probe resistance value, but the issue of signal-to-noise ratio still remains. Therefore, the employment of multichannel preamplifier(s) is still preferable.

In a preferable modification of the invention, there is provided a series condenser at the input to each of the amplifier channels for picking up substantially and exclusively the occurred changes in the body surface potentials for amplification, although not shown. In this way, possible signal errors due to unstable conditions at the body surface can substantially be removed.

These multiplexers 3A and 3B are so arranged as to pick up sensed output signals from respective probes successively and to feed them to the next following AD-converter 4.

The AD-converter operates so that the output signals sensed at the probes and picked up successively by the multiplexers 3A and 3B are converted from analogue to corresponding digital signals which are in the preferred embodiment of the invention in 8- or 16-bits. It is sufficient to treat those signals of relatively low frequency components as is the case for the PQRS-loop or T-loop of the normal cardiograph as illustrated at (I) of FIG. 8, with 8-bits. When there are small and fine rhytmic waves as at QR-loop and as appearing in a patient suffering from myocardinal infarction, the sensed potential signal includes rather higher frequency components, and use of 16-bit conversion is recommended. Anyhow, there is utilized as the parity bit one of the said 8- or 16-bit converted signals, for adjudging the input signal to be either of minus or plus value. Digital output signals from AD-converter 4 are then fed to IC-memory 5 for accumulation therein.

Since a heart beat extends for about a second, and when assuming that a functional cycle including a certain pause period extends for 2 ms, such cycles will repeated 500 times within the perior of a heart beat. When further assuming that a cardiographic observation is once executed for 10 minutes, all the measured data can be preserved provisionally in an IC-memory having a memory area as covering: 60×10×500=300 kilobits. When the IC-memory has a capacity of one megabite, the said value of necessary bits corresponds to about one third of the memory capacity.

Figures 9, 11, 12:
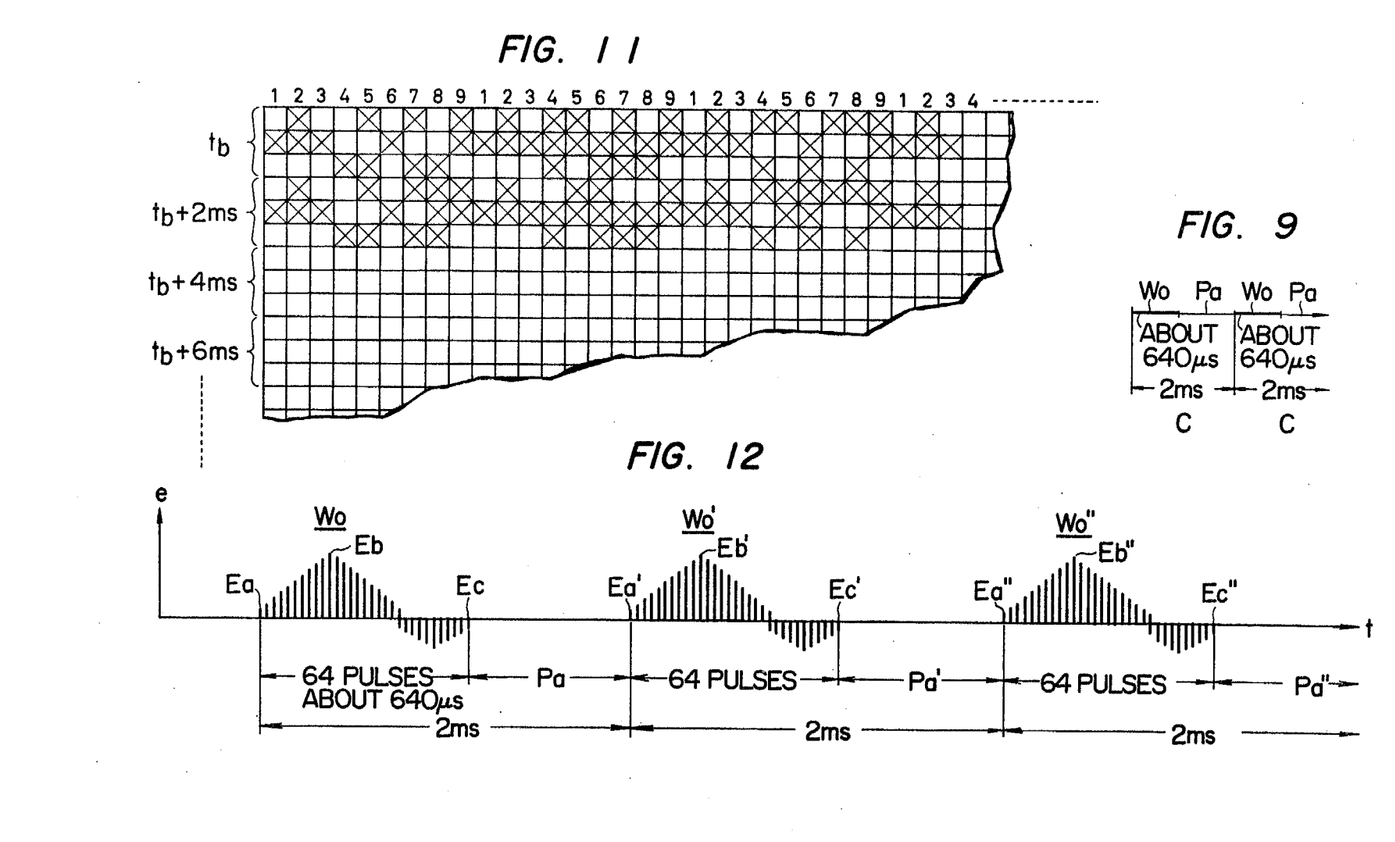
FIG. 9 is a schematic diagram showing a signal sensing period WO and the next following pause period Pa in which signal modifying treatments are carried out.
FIG. 11 is a schematic diagram showing a number of addresses contained in the IC-memory and preserving a part of the output digital signals delivered from the AD-converter and shown in FIG. 10.
FIG. 12 is a schematic and somewhat modelized diagram of an analogue signal which substantially corresponds to the digital signal shown in FIG. 10.

When assuming that about 10 μs is set for signal treatment set forth hereinbefore and per one probe under considering the sensing time constant for each probe and the presently and commonly utilized performance of the AD-converter, the time for successive take-out of signals from all 64 channels will be substantially 10×64=640 μs. Further necessary measurements and signal treatments are carried out by the help of a microcomputer 6. For this service, a time period of about 1,300 μs is necessary. For this reason, and as schematically illustrated in FIG. 9, one functional cycle period has been set to 2 ms. Thus, for completing the said functional cycle and returning to the original and first probe, multiplexers 3A and 3B are controlled.

Control signals delivered from control section 5a contained in the IC-memory 5 are conveyed through first control circuit 7 and second control circuits 8A and 8B to multiplexers 3A and 3B for operating the latter step by step. More specifically, the sensed and amplified signals are treated by the circuits following the multiplexers and all the necessary circuits become ready for accepting the next following signal, the multiplexers being actuated for initiating the next step.

Outputs of IC-memory 5 are connected to microcomputer 6 and first control circuit 7, while outputs of the latter are connected in parallel to second control circuits 8A and 8B which are inserted in the A-series and the B-series of the signal processing route, respectively, to AD-converter 4 and monitor amplifier 9, respectively. A combined comparator and interpolator circuit 90 is connected between AD-converter 4 and IC-memory 5.

The microcomputer 6 comprises a clock signal section 6a designed and arranged to operate at 2097 kHz and the cyclic operation repeated at each 2 ms for probe signal read-out, as was referred to hereinbefore, is initiated with each 2 ms-trigger or clock pulse issued from the clock signal section 6a.

Referring to FIG. 9, the operating cycle is shown by C which cycle extends for 2 ms and comprises a signal sensing and read-out period W0, each extending to substantially about 640 μs, and residual pause period Pa. During the latter period Pa, occasionally required incorrect signal removal job(s) and the substitution of correctly assumed signal(s) may be executed.

The microcomputer 6 performs the following several jobs in cooperation with the related circuits 5, 6a and the like.

(a) control of the whole system;
(b) selection and offsetting of zero potential level of sensed signals;
(c) establishment of proper time correlation between heart pulses and sensed signals;
(d) shooting of incorrectly working probes and provisional removal of related signal processing channels if the contact resistance and contact potential difference fluctuates substantially and the resultant noise signal frequency enters the working frequency band of the preamplifier ranging normally from 0.2 to 300 Hz;
(e) shooting of incorrectly operating preamplifier(s) and provisional removal of the related channel(s);
(f) finding of error signals caused by such as the source hum and inductive disturbances, and removal of false signals in vicinity of the found error signals of the sensed signal series;
(g) linear and space interpolation of the sensed signal series;
(h) detection of occasionally possible high frequency components of the heart beat as caused by extraordinary rhythmic movements and a specific and detailed display of sensed signals including those of these movements;
(i) calculation and display of the variance;
(j) calculation and display of the coherence;
(k) calculation and display of a coherence map;
(l) calculation and display of a spectrum map in relation to a specifically specified frequency;
(m) comparative displays of input data after lapse of a selected time interval of several hours, days and months;
(n) calculation and display of the mean value during a measuring cycle at each probe, for instance, for a heart beat;
(o) selection and comparison of any sample signal;
(p) execution of sample-holding or its equivalent signal processing.

In such a case where the input signal varies considerably in comparison with the measuring period or in its similar case, the sample holding or signal after-treatment substantially equivalent must be employed.

As a recommendable way for the sample-holding, signals may be fed from the microcomputer 6 to the preamplifier so as to hold the signal data. As a preferred mode of the after-treatment, the data preserved in IC-memory 5 are reviewed and the time lag at each succeeding probe, amounting to 10 μs as employed in the embodiment shown in FIGS. 5 and 6, is adjusted in the proper way.

In the latter case, each of the sensed and preserved data is timely adjusted to the corresponding preceding one by means of the microcomputer 6 and for each probe and reintroduced in the IC-memory 5 at its remaining unused area, so as to be used in the signal processing.

Generally speaking, if the sample-holding procedure is adopted and the data are held for a relatively long period, there will be a tendency to overlook fine and delicate progress of the signal appearing in the operational cycle C which extends for 2 ms in the case of FIG. 9. Therefore, reliance should preferably be made on the aforementioned signal after-treatment procedure.

The "control of the whole system" as mentioned hereinbefore at item (a) includes the issuance of the instructions for the "initiation of measurement", for "counter clearing" of multiplexers 3A, 3B since these multiplexers include electronic counters which operate to shift stepwise the measuring probes by each one in the successive order) and for initiating each measuring period W0 shown by a thick line in FIG. 9.

In addition, the microcomputer 6 is so designed and arranged as to establish proper time correlation between heart pulses and sensed signals, and for signal after-treatments and calculations, as indicated in the foregoing items (c) and the like.

Figure 10:
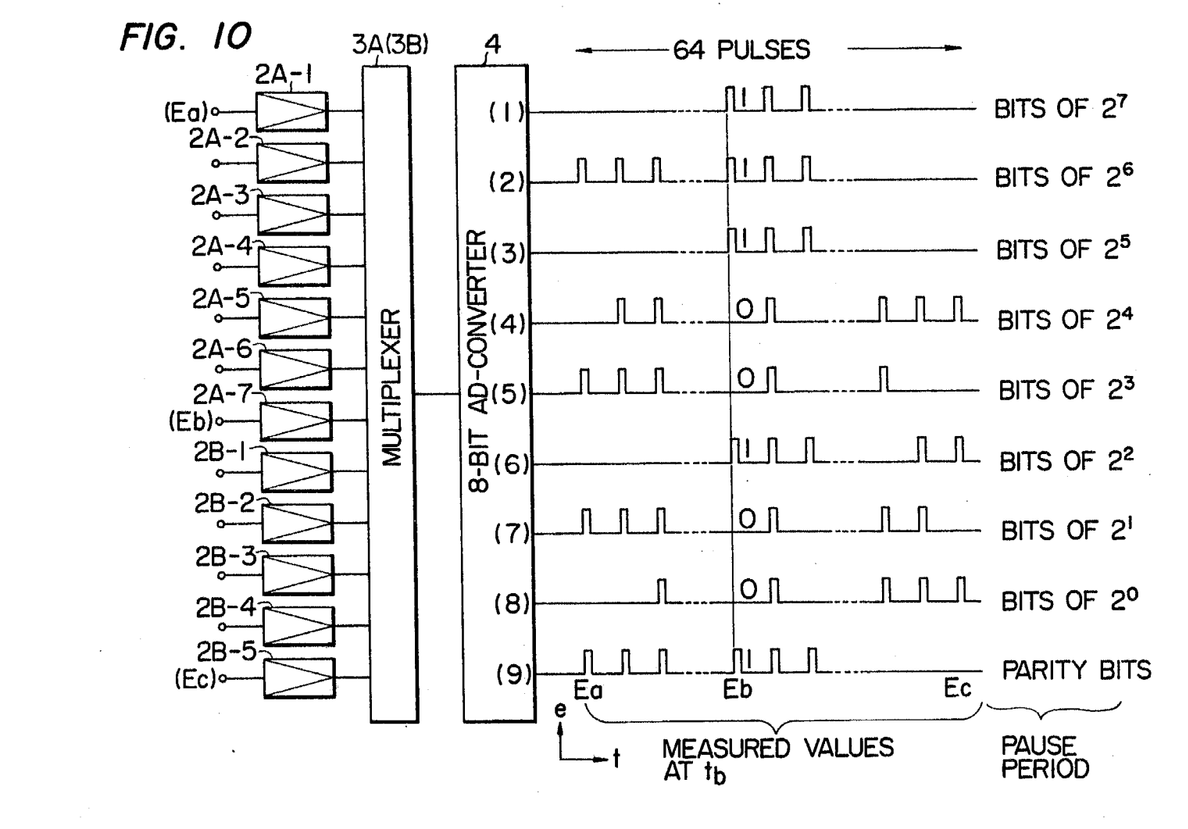
FIG. 10 is a schematic view mainly representing a schematic sample of output digital signals delivered from the AD-converter.

A perferred embodiment of signal after-treatment will be set forth with reference to FIGS. 8; 10 and 11.

In FIG. 10, a number of preamplifier elements 2A-1, ... 2A-7; 2B-1, ... 2B-2, ... 2B-5, representatively constitute the preamplifiers 2A and 2B, respectively.

Although, in fact, 64 preamplifier elements are provided, its number has been simplified only to 12.

Figure 8:
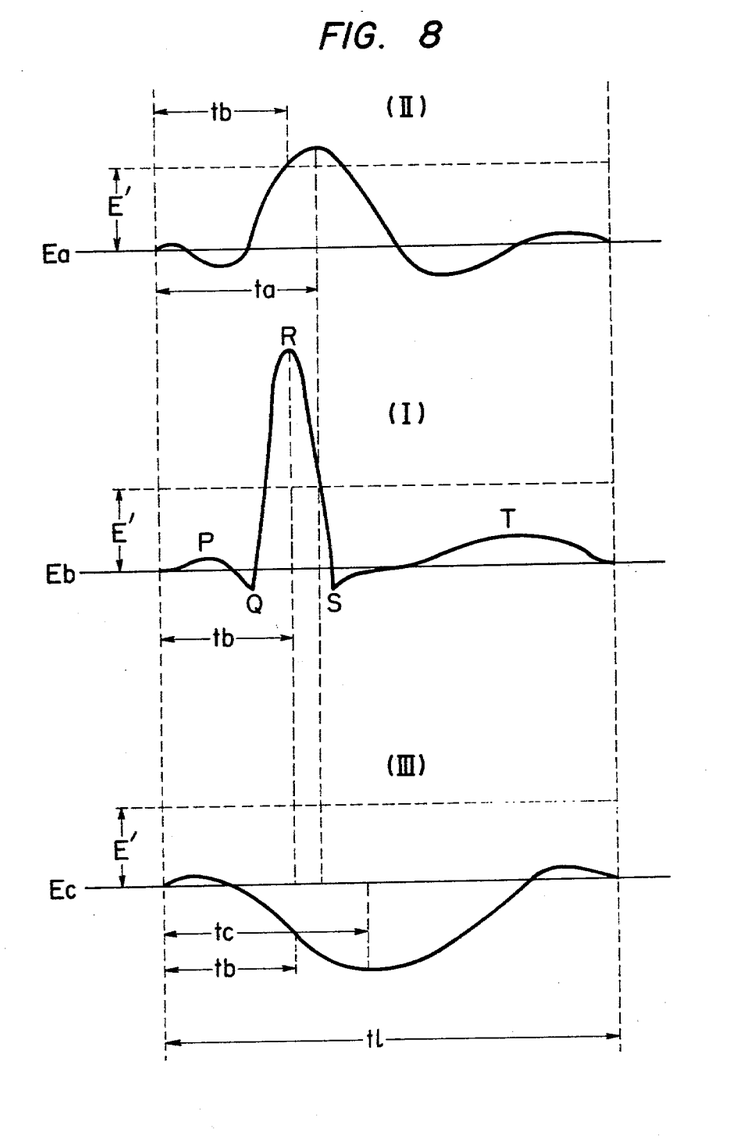
FIG. 8 represents conventional cardiographs (I), (II) and (III) taken at three different positions in vicinity of the heart of the patient.

In FIG. 8 at (I), the thick curve represents a cardiograph Ea similar to the normal one and sensed at a probe placed on the body surface and above the heart of a person.

FIG. 8 at (II) represents a sensed cardiographic potential curve Eb sensed at a probe which is placed at an upper right position relative to the heart and set on his breast.

FIG. 8 at (III) represents a further cardiographic potential curve Ec sensed by a still further probed placed at a lower left position on the breast.

The sensed potentials at all the probes are fed through the respective preamplifier elements and multiplexers 3A, 3B to AD-converter 4 of 8-bit type. From the respective output channels (1)-(8) of the AD- converter, the converted digital pulses are delivered, as shown in a modelized manner at the right hand side of FIG. 10. The additional bits delivered from the final output channel (9) is utilized for identification of the symbol "plus" or "minus" of the signal, thus constituting "Parity bits".

At a certain measuring time, the sensed potential Ea may be "010010101"; Eb: "111001001" and Ec: "00110110", as an example.

The digital value "111001001" of Eb at this moment is represented by $+(128+64+32+0+0+4+0+0)$, thus with its effective three figures representing "228" units. This value can be seen by upwardly following a vertical line established at Eb in FIG. 10.

The values of Ea and Ec may similarly be seen.

In FIG. 11, part of the addresses of IC-memory 5 is shown in a highly modelized manner and how the bits shown in FIG. 10 have been written-in. In this FIG. 11, the cross-marked addresses are those which have been charged each with a "1"-digit, while all the blanked addresses are those which have been charged each with a "0"-digit. However, it should be noted that substantially an upper half of the shown addresses are shown as charged with bits for memory, while the remaining lower addresses are shown in their unused state.

In FIG. 12, three successive groups of the sensed analogue signals are shown only schematically and in a rough sketch which corresponds to those shown in the digital manner in FIG. 10. The ordinate e represents the sensed potential, while the abscissa denote the time, wherein, however, both are shown in arbitrary scales for the demonstration of substantial inclination of sensed potentials only.

The values of Ea, Eb and Ec in FIG. 8 take their respective peaks at $t_b$, $t_a$ and $t_c$. By reviewing these waves at (I), (II) and (III), it will be easily imagined that excitement of the heart is subjected to polarization and rotation.

It would be possible to hold the sensed and preamplified information signals and then to take them out, subjected to various treatments for proper display of the sensed results. In this case, however, the time constants of the circuits, having a relationship to the cyclic operation necessary for subjecting the sensed signals, at the first to the final probe, to necessary signal treatments, would become larger than expected and, thus, the cyclic operation as a whole would amount to 10 ms as an example in the present case using 64 probes placed on one body surface of the patient, resulting in a rather longer measuring cyclic period. This will naturally result in a kind of skipping in the measuring operation which is thus substantially discontinuous.

In a preferred embodiment of the invention, a short time period such as about 10 μs, is attributed to each probe and thus, 640 μs as a whole are required for reading out the sensed probe signals from the multiplexer for completion of one cycle of probe measuring operations covering the said 64 probes. It will thus be seen that all the read-outs for the group of probes are not taken simultaneously when seen theoretically, but in fact successively 10 μs-interval per each probe will be required. In comparison with each heart pulse which may be assumed to be in the order of one second, such a short time lag as 10 μs, which may be deemed as a kind of high frequency, represents no inferior influence upon the required precise measurement, and thus neglegible in the practice of electronic diagnosis. In the following, substantially a preferred embodiment will be set forth in the above sense.

As briefly referred to hereinbefore and as for $E_a$, $E_b$ and $E_c$ shown in FIGS. 8 and 12, $E_a$ represents apparent nil potential level appearing at a probe positioned at the upper left corner of the probe-distributed area; $E_b$ represents that of a probe positioned centrally above the patient's heart; and $E_c$ is that of a further probe positioned at the lower right corner of the same area. These probe potentials are shown at three successive measuring cycles and in an analogue manner in FIG. 12, wherein the first, second and third probe signals are shown at $E_a$, $E_b$ and $E_c$; $E_a'$, $E_b'$ and $E_c'$ and $E_a''$, $E_b''$ and $E_c''$; respectively.

As shown, there are pause period Pa and Pa' among the truely functional periods $W_O$, $W_O'$ and $W_O''$.

Although no signal comparison job is made during the first pause period Pa, such comparison is made during each of the next following pause periods.

According to our experiment, the maximum potential fluctuation will be less than a maximum of 5% or so, when taking 2 ms as one probe measurement cycle for 64 probes and as a rough measure; in practice, this fluctuation is far less than the above estimated rough maximum value. It can be safely assumed that, if the fluctuation in the measured potentials should be higher than the value, certain measured signal or signals may include excessive noises, and thus they must be excluded. And in place thereof, estimated value(s) is(are) inserted. This kind of signal correction may be called "linear interpolation in virtue of time sequence of measurement".

Next, the manner of establishing and selecting potential level will be described in detail.

This job is performed based on the memorized signal data at the IC-memory 5. However, these data have been subjected to all the troubles mentioned in the foregoing several items (d), (e) and (f), concerning the probes and preamplifier, and subjected to correction executed at each pause period $P_a$ or the like.

The analogue data shown in FIG. 12 correspond to those measured and memorized data which represent signal variations appearing at three substantially remote probes.

On the other hand, according to our experiments, the signal-exciting source or the patient's heart may be deemed definitely at its maximally excited state if one third of the whole probes or 21 probes thereof are shown simultaneously at certain potentials higher than a predetermined voltage level such as 3 milivolts.

When this time point or instance is signified by R, the operator has given operation instructions to the microcomputer 6 to read out the time which is foregoing, by 60–100 ms as an example, from the said critical time point R. Next, the memorized values during a specifically selected short time period such as 10 ms measured before and after such time point as corresponding to the newly read-out foregoing time differential and at each measuring point are read out. Three values are equivalenced for finding the mean, which is used as the zero potential level during the next following measuring cycle covering all the measuring probes. In this way, the nil potential level is variable when seen over the total measuring job and, normally, for each measuring cycle over all the probes, a newly selected and corrected level is set and utilized. This data level correction job may be called "offsetting".

For each measuring cycle, all the data are offset based on the newly established and corrected nil level, and then put into new and empty addresses of the IC-memory 5. If the nil potential level varies unintentionally and substantially for a long time, such as several minutes, a disadvantageous and harmful drift may be present. However, by use of the foregoing offsetting, adverse effects of the drift may be effectively and automatically avoided, although the practical nil potential level may vary during each measuring cycle.

At the color display unit 12, with two color tones, preferably red and green, the measured signals may be displayed. The red color displays represent positive signals, while the green one shows negative signals. By adopting the foregoing off-setting procedure, the color display may represent a fine and clear color tone on the display screen.

As for the interpolation procedure set forth hereinbefore at item (g), there are two kinds of operations, one being the linear interpolation already referred to herein and the other being the areal interpolation to be described.

Although repeating, the linear interpolation is only briefly mentioned. In accordance with this procedure, the interpolation is performed on the information data removed of extraordinarilly deviated noises as already mentioned at the foregoing items (d), (e) and (f). This kind of interpolation procedure has been specifically described hereinabove. As a brief conclusion, it should be noted that those extraordinarily deviated sensed signals containing excessively large noises are removed automatically from the signal series. For avoiding difficulties and inconvenience caused by such intentional dropouts and appearing in the next following signal processing and display stages on account of the presence of the thereby caused discontinuity in the signal series, the linear interpolation is executed for the sake of completing the latter.

In this way, all the sensed signal series are supervised automatically by the microcomputer 6 and, if there be a dropout signal at (n+1)th probe position as an example, the corresponding signal is intentionally and automatically calculated for interpolation. If such interpolation should not be executed, the (n+1)th signal will take the same value as that of the foregoing n-th signal during the following signal processing stages, and thereby the measured and processed value become inaccurate and the display is subject to deficiency rather than otherwise.

As for the areal interpolation, the procedure is so executed that the number of the sensing probes is increased without increasing the real probes and, indeed, by execution of a real interpolation procedure(s).

It may naturally be expected to have better and more accurate sensed results by increasing the practical number of the sensing probes substantially to an indefinite degree, for measuring observation of the characteristics of bioelectrical phenomenon. But, in practice, the probe number is substantially limited by reason of the difficulty in the attaching technique of the increased and crowded probes onto the patient's body. In addition, rather substantial and frequent noise signals will be invited and the measured results may be disturbed.

Internal and additional electrical troubles may be rather encountered by virtue of complexity of the electrical circuits contained. As an example, provision of 8×8=64 probes may be the most condensed arrangement thereof from the practical convenience. However, for attaining more reliable and accurate measurement and display, the provision of more numerous probes would be necessary to adopt, if adjudging from our practical experiments.

As an example, each side of a square or rectangle defined by neighboring four probes is divided to eight divisions by performing linear interpolations. And then, an areal interpolation is carried out to provide an additional, but imaginary, network-like probe arrangement within the said area defined by the four original and practical probes. Further, if necessary, a further and higher dimensional interpolation job may be executed in the similar manner, as may occur to any person skilled in the art after reading the foregoing disclosure of the interpolation.

The foregoing interpolation is executed in accordance with the sampling theorem. In the present embodiment, using 64 probes provided at one surface of the patient, and as for those components the half wave length of which is larger than the interelectrode distance, the internal and electrical potential $\phi(x; y)$ at any selected point $(x; y)$ within the probed area defined by the outermost rows and lines of the probes may be correctly determined by the following general formula:

$$\phi(x; y) = \sum_{m=1}^{8} \sum_{n=1}^{8} \phi(m; n) \cdot \frac{\sin\left\{8\pi(x - \frac{m}{8})\right\} \sin\left\{8\pi(y - \frac{n}{8})\right\}}{8\pi(x - \frac{m}{8}) \, 8\pi(x - \frac{n}{8})}$$

where, $\phi(m; n)$ represents the calculated electrical potential attributed to an interpolated point: $(m; n)$.

In order to make a color display of the measured and processed signals by means of color display unit 12 shown in FIG. 7, positive and negative potentials derived from IC-memory 5 are each classified to eight stages and the picture elements are adjusted to correspond thereto by the brillance modulation. In this way, the positive potentials are displayed with different red color tones, while the negative potentials are shown with different degree color tones. Naturally, the potential peak is displayed each by the maximum brilliance By reviewing the shape and position of the red and green display images and those of black images corresponding to nil potential ranges and positions defined by and between the margins of the both color images, precise clinical judgment can be made with ease. Especially, the areal scope, and degree and depth of the color tone, can permit a detailed and specific clinical judgement to be made.

The display unit is illustrated only generally by a single block wherein a character display 13 is provided in parallel to the said color display 12. Therefore, a character display can be made in place of the two color display. Busing the character display, the display can be executed by means of characters and in place of colors. As an example, the signal values are calculated in the form of square deviation and transformed into ten step digits 0–9 for printing on a paper with these classified characters.

Within the display unit, a cassette MT 14 and a flexible disc 15 are provided in parallel. Cassette MT 14 can be used for preservation of the sensed data and, when necessary, the latter may be taken out for reuse, that is, for the purposes of comparison or repeated usage. It comprises naturally a coil magnetic tape.

The flexible disc 15 is utilized for separated and provisional preservation of part or all of the memorized contents of IC-memory 5.

By using a monitor amplifier circuit 9 and an oscilloscope 10, part of the signals may be taken out at any stage for supervision.

Figure 13:
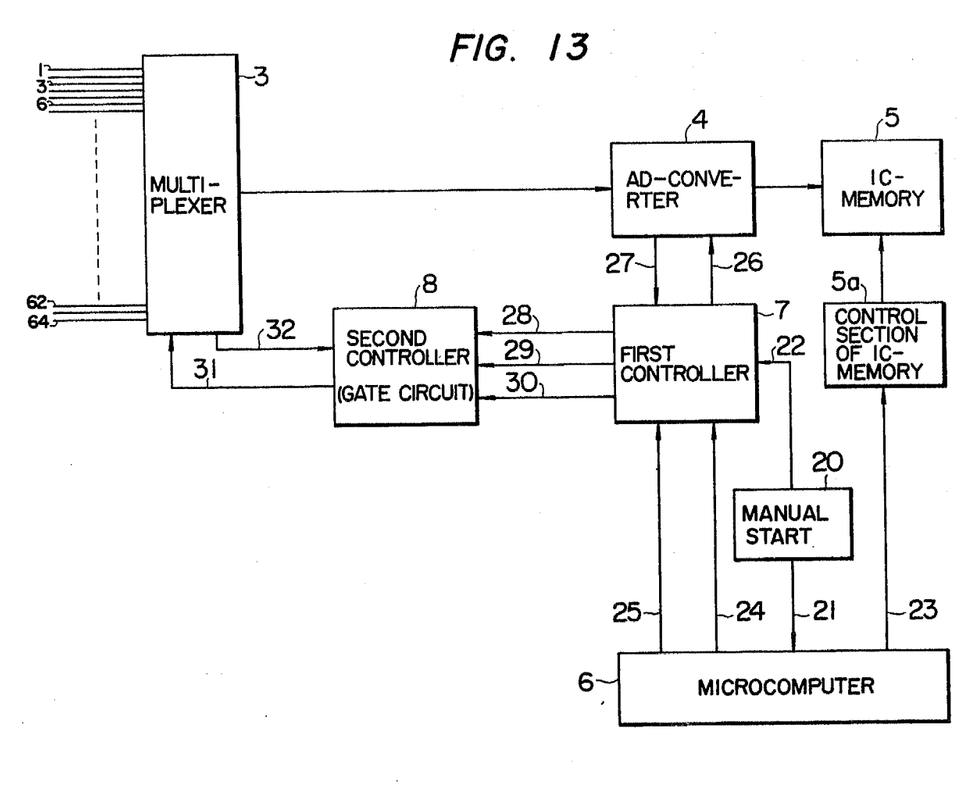
FIG. 13 is a modified representation of part of the block diagram of FIG. 7, specifically showing the function of the first and second control circuits.

In the arrangement shown in FIG. 13, as somewhat modified and simplified from that of FIG. 7, first and second control circuits 8A and 8B have been shown as united into one, but related circuit connection routes have been more specifically shown for the illustration of the foregoing signal after-treatment procedures.

In addition, the foregoing multiplexers 3A and 3B have also been united into one single block 3. In this FIG. 13, numeral 4 represents an AD-converter and 5 and IC-memory, as before. For control of the latter, a control section 5a thereof is shown specifically in a separated form for easy understanding. Reference numeral 6 indicates a microcomputer, as before.

Numeral 20 represents a manual start member which is more specifically an on-off switch. By closing this swtich, microcomputer 6 and first control circuit 7 turn to on. The first control circuit 7 may be a C-MOS comprising a signal amplifier, and a frequency divider which may be a series of flip-flops.

Microcomputer 6 has an outlet for delivery of an address-designation signal to IC-memory 5 through lead 23, and more specifically to control section 5a of the latter. By the delivery of such designation signal, a specifically selected address of IC-memory is specified.

First control circuit 7 is connected with microcomputer by means of leads 24 and 25, and more specifically, clock signals of 2 ms-frequency are delivered through lead 24 and data hold signals are received through lead 25.

First control circuit 7 is connected through leads 26 and 27 with AD-converter 4. More specifically, start instruction signals are fed via lead 26 and termination instruction signals are delivered through lead 27.

First control circuit 7 is connected through leads 28, 29 and 30 to second control circuit 8 which may be a gate circuit of known structure. From the first control circuit 7, on AD-conversion termination instruction is fed through lead 28, clock signals of 2 ms are conveyed through lead 29; and a data hold instruction is fed through lead 30.

Second control circuit 8 is connected through leads 31 and 32 to the multiplexer. More specifically, step-up signals are fed through lead 31 and a function termination instruction is fed through 32.

Figure 14:
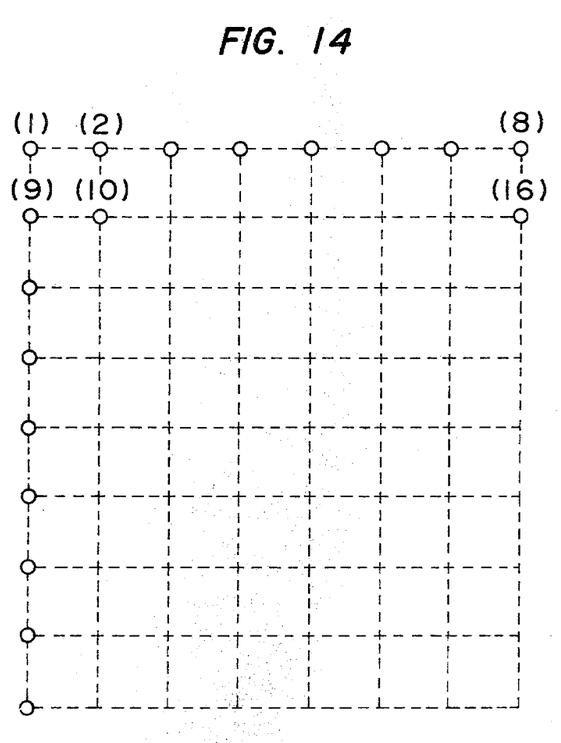
FIG. 14 is a schematic graph of a local arrangement of a limited number of the probes for showing the mode of the interpolation.

In the following, the areal interpolation will be described still more specifically with reference to FIG. 14 showing an area defined by 8×8=64 probes.

At first, the microcomputer 6 calculates the mean value of certain sensed values at the first and second probes (1) and (2). At the present stage, a time lag of 10 μs appearing between these two probes has been and will be omitted only for simplified description. This mean value point is shown at (110) in FIG. 15. Then, the mean value between (1) and (110) is found and plotted at (111), and that between (110) and (2) is found and plotted at (112). A kind of four divisional interpolation has thus been realized between (1) and (2). In a similar manner by equidivision, additional points (113), (114),(115) and (116) are fixed. IN this way, an eight divisional interpolation has been completed between (1) and (2).

Figure 15:
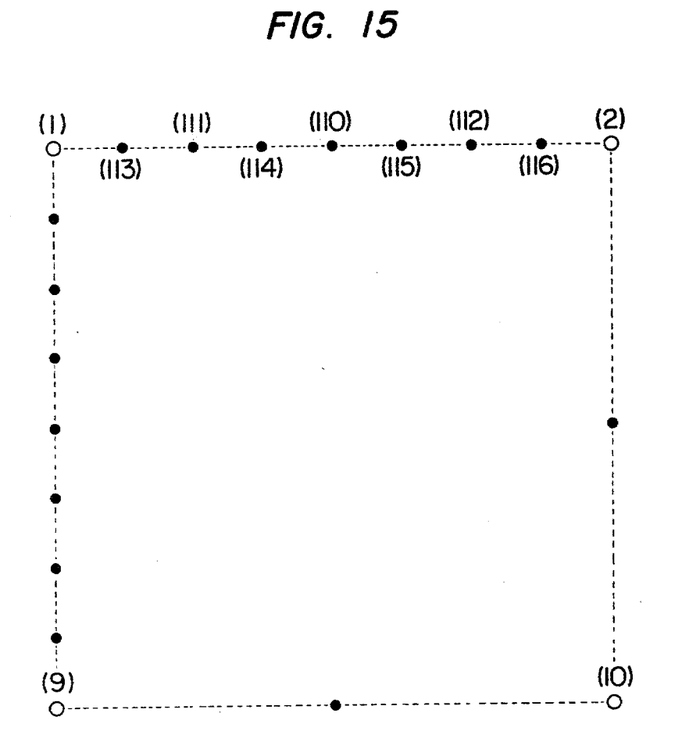
FIG. 15 is a similar and detailed graph of a part of FIG. 14 for further clarifying the interpolation.

Similar eight divisional interpolation is then performed between (1) and (9), and further between (2) and (10) and still further between (9) and (10). In this way, all four sides of a small square or rectngular divisional area defined by four probes (1), (2), (10) and (9) are each subjected to a linear interpolation.

Then, by operating the microcomputer 6, an imaginarily probe-sensed value to appear at each cross point of the horizontal and vertical divisional lines is calculated for execution of the scheduled areal, or more specifically spatial interpolation.

Then, similar procedures are carried out for all the divisional areas, each defined equally by practical and imaginary four neighboring probes. However, on occasion, certain of these spatial interpolation procedures may be dispensed with.

This kind of spatial interpolation procedure is highly effective and valuable for providing a distinct, beautiful color picture of the measured values with use of an ample number of picture elements. Without use of this kind of spatial interpolation, the picture will be made of only 64 "islands" in correspondence with the number of the real measuring probes. With use of the spatial interpolation, the number of "islands" will be 64×64, and thus the color display will be made with an ample number of picture elements for providing a clear and characterizing color picture, suitable enough for the scheduled purpose.

The corresponding digital display at 13 may be made with eight red color stages, and equally with eight green color stages. For diagnostic purposes, heart diseased persons are naturally of most concern, and it should be stressed that disease signals are generally generated, so to speak, suddenly and locally. It was considerably difficult to discriminate these disease signals from noise signals, when reliance was made upon conventional apparatuses. However, with the novel apparatus according to the present invention, such discrimination can be realized without difficulty.

Several multifunctional effects of the inventive apparatus will be set forth in the following.

Since noises, caused by possible attaching and positional errors at the probes, and internal circuit disturbances have been substantially removed from the measured surface potential signals, and the latter has been interpolated to a satisfying degree, the position of QRS-peak can be detected quite easily. The procedures are:

(i) After acknowledgement of the removal of noises, determine such a point where the measured values at three consecutive probes become higher than a predetermined level, such as 8, when the proven voltages are classified in accordance with 128 stages.

(ii) Determine such a time point where a certain number, such as $\frac{1}{3}$, of the total real probes satisfy the above condition. This time point may be that of the QRS-peak.

(iii) Next determine such a foregoing point of time by a predetermined time length, such as 100 ms, and take the mean value of those of these three points thereat.

The value 100 ms may vary depending upon the personality, but only slightly. But, this value can easily and promptly be detected by delivering the signal data through monitor amplifier 9 to oscilloscope 10 and reviewing the picture.

In this way, substantially correct nil potential level can be detected.

It is also possible to display an instantaneous potential map at such a point as elapsing a predetermined time period, such as 40–80 ms, counted from the above determined QRS-peak.

This procedure is highly effective for detecting abnormal conditions at an auxiliary transmission system in the case of WPW-syndrome. It is easy to determine the location of the abnormal position by review of the red and green images on the display screen which is highly convenient for execution of surgical cutting operation of the Kent bundle.

The above display procedure may be mathematically expressed by the following general formula:

$$\frac{1}{n-m} \sum_{l=m}^{n} \phi_j(t_c)$$

where, j denotes the number of probe.

In order to find the variance, the following formula can be used.

$$\frac{1}{n-m} \sum_{l=m}^{n} \phi_j(t_e) = \overline{\phi_j} \text{ (mean value)}$$

$$\frac{1}{n-m} \sum_{l=m}^{n} \phi_j^2(t_e) = \overline{\phi_j^2} \text{ (sequare mean)}$$

The variance of $\phi_j \equiv \overline{\phi_j^2} - (\overline{\phi_j})^2$

For finding the coherence spectrum, the following formula can be used:

$$S_j(f) \equiv \frac{1}{(n-m)\Delta t} \sum_{l=m} \phi_j \exp[2\pi f \cdot t_e]$$

More specifically, the value of $$\frac{S_j(f) S_i(f)}{|S_j(f) S_i(f)|}$$

is found for ten heart strokes and summed up to find the means in its absolute value.

Thus, the variance map is that showing the body surface potential activity in terms of square deviation.

With the normal heart conditions, the variance map of the QRS-wave represents a substantially similar type as that of T-wave, and the peaks appear in close proximity to the heart.

When the heart is subject to myocardial infarction, the QRS-variance map takes a different shape from that of T-wave. It will be seen that, in this case, there are myocardial impediment and infarction.

If there are transmission impediment and cardiac hypertrophia, the QRS-variance map and T-variance map take a similar type of configuration, but they are different from the normal shape. In this case, there is no cardial infarcation.

For finding the correlation map, the following general formula is utilized and a calculation plotting is made from i to j, by taking the i as the base.

$$\frac{\sum_{l=m}^{n} \phi_j(t_e) \phi_i(t_e)}{\sqrt{\left(\sum_{l=m}^{n} \phi_j^2(t_e)\right)\left(\sum_{l=m}^{n} \phi_i^2(t_e)\right)}}$$

On the other hand, for finding the spectrum map, the following formula:

$$\frac{1}{(n-m)\Delta t} \left| \sum_{l=m}^{n} \phi_j(t_e) \right|^2 \exp[2\pi f t_e]^2$$

and calculation and plotting are made to plot the value at j.

By reviewing the progress of the potential map obtained by use of the inventive apparatus, the following clinic operations are carred into effect, in addition to those hereinbefore shown and described.

I. Existence of "leg block", if any, can be found by observation of a specific configuration of the red color representations at the T-curve portion upon lapse of the QRS-curve.

II. Existence of cardiac infarcation, if any, and the location thereof can be made by observing the position of green images at the initial region of the QRS-curve portion.

III. By finding the variance of potential variation at all the sensing points throughout a heart pulse, and by representing the contour line preferably in red on the variance map, the area thereof will show the degree of the cardiac infarcation.

IV. At the same time from the variance map, the impedance distribution between the heart and the body surface can be observed. If there be a substantial abnormality in the impedance distribution, cancer or a similarly extraordinary disease could be detected.

V. By observing the area and brightness of red images at the ST-region, the degree of affection by acute cardial infarcation can be detected. By observation of a lowered level of ST-wave, one can determine that there are non-specific ST-abnormality and ischemic ST-abnormality. It was highly difficulty to discriminate between the two with use of conventional apparatus. However, by use of the inventive apparatus, it will be observed that, in the former, the ST-curve is lowered in its level, but shows no localized configuration and, when the observed signals are displayed in color, additional green images will be seen in the lower area near the patient's abdomen. In the latter, green images appear at a part of the heart, and the corresponding ST-curve is lowered at its level, on account of the fact that the blood is not conveyed to the heart coronary arteries.

VI. By observing a specific configuration of the QRS-region, minor myocardial affections may be detected at an early stage.

VII. It is possible to realize an automatic clinic operation from the surface potential display to detect various heart diseases and to show the latter in color codes.

The embodiments of the invention in which an exclusive property or privilege is claimed are as follows:

1. An electronic clinic apparatus, comprising in combination:
    a group of a number of probes positioned in proximity to at least one body surface of a person subjected to a clinic operation;
    a multichannel amplifier for amplifying electrical potential sensed at each of said probes and having an output;
    a multiplexer connected to said amplifier at said output of said amplifier, and having analog outputs;
    converter means connected to said multiplexer for converting said analog outputs of said multiplexer to corresponding digital outputs;
    computer means for processing said corresponding digital outputs of said converter means to produce outputs of said computer means;
    display means for displaying said outputs produced by said computer means; and
    control means provided between said multiplexer and said computer means for successively reading out the sensed potentials at the probes within a variable operating period and for providing a pause period thereafter, said variable operating period being added with said pause period to define a predetermined functional cycle period, said control means intentionally removing improper probe signals including excessively large noise signals and replenishing properly calculated and established imaginary signals in place thereof, said removal and replenishing functions being performed during said pause period.

2. The electronic clinic apparatus of claim 1, wherein said probe is a directly contacting electrode attached in a removably fixed state onto the body surface of said person by means of an adhesive agent.

3. The electronic clinic apparatus of claim 1, wherein said probes are assembled together at least into a unit comprising an insulating and flexible sheet perforated with a number of separated holes, each of the separated holes being fitted with a probe.

4. The electronic clinic apparatus of claim 1, wherein each of said probes is an electromagnetic sensor positioned at a certain predetermined distance from the body surface.

5. The electronic clinic apparatus of claim 1, wherein each of said probes and one of said amplifier channels are integrated into one unit.

6. The electronic clinic apparatus of claim 1, wherein said probe is a directly contacting electrode attached in a removably fixed state onto the body surface of said person by means of an adhesive tape.

* * * * *